US008673865B2

(12) United States Patent
Ueno et al.

(10) Patent No.: US 8,673,865 B2
(45) Date of Patent: Mar. 18, 2014

(54) AGENT FOR ENHANCING ANTISEPTIC POWER

(75) Inventors: Katsuya Ueno, Wakayama (JP); Hiromoto Mizushima, Wakayama (JP); Hiromi Kubota, Tochigi (JP); Katsumi Endo, Tokyo (JP)

(73) Assignee: Kao Corporation, Tokyo (JP)

( * ) Notice: Subject to any disclaimer, the term of this patent is extended or adjusted under 35 U.S.C. 154(b) by 1399 days.

(21) Appl. No.: 11/885,387

(22) PCT Filed: Feb. 27, 2006

(86) PCT No.: PCT/JP2006/003579
§ 371 (c)(1),
(2), (4) Date: Jun. 10, 2008

(87) PCT Pub. No.: WO2006/100874
PCT Pub. Date: Sep. 28, 2006

(65) Prior Publication Data
US 2009/0156511 A1  Jun. 18, 2009

(30) Foreign Application Priority Data
Mar. 3, 2005 (JP) ................................ 2005-058634

(51) Int. Cl.
*A01N 43/04* (2006.01)
*A01N 31/00* (2006.01)
*A01N 31/08* (2006.01)
*A61K 31/70* (2006.01)
*A61K 31/045* (2006.01)
*A61K 31/05* (2006.01)

(52) U.S. Cl.
USPC ................................ 514/25; 14/724; 14/731

(58) Field of Classification Search
USPC .......................... 514/25, 724, 731
See application file for complete search history.

(56) References Cited

U.S. PATENT DOCUMENTS

| H224 H | 3/1987 | Malik et al. |
|---|---|---|
| 4,920,100 A | 4/1990 | Lehmann et al. |
| 5,498,704 A * | 3/1996 | Wolf et al. ................ 536/18.6 |
| 5,521,293 A * | 5/1996 | Vermeer et al. ............ 536/17.2 |
| 5,591,376 A * | 1/1997 | Kiewert et al. .............. 510/437 |
| 5,641,480 A * | 6/1997 | Vermeer .................. 424/70.24 |

FOREIGN PATENT DOCUMENTS

| EP | 0 551 674 A1 | 7/1993 |
|---|---|---|
| GB | 2 362 320 A | 11/2001 |
| JP | 5-43403 A | 2/1993 |
| JP | 2004-175846 A | 6/2004 |
| WO | WO 86/04899 A1 | 8/1986 |

OTHER PUBLICATIONS

Matsumura, S., Imai, K., Yoshikawa, S., Kawada, K., Uchibori, T. (1990) Surface Activities, Biodegradability and Antimicrobial Properties of n-Alkyl Glucosides, Mannosides and Galactosides. Journal of the American Oil Chemists Society, vol. 67, No. 12, p. 996-1001.*
Supplementary European Search Report issued on Sep. 14, 2010 in corresponding European Patent Application No. 06 71 4716.

* cited by examiner

*Primary Examiner* — Scarlett Goon
(74) *Attorney, Agent, or Firm* — Birch, Stewart, Kolasch & Birch, LLP

(57) ABSTRACT

The present invention relates to a preservative efficacy-enhancing agent capable of allowing an antiseptic agent to exhibit a high preservative efficacy even when the antiseptic agent is used at a low concentration; a preservative efficacy-enhancing composition containing the same; and a method for enhancing a preservative efficacy of antiseptic agents. The present invention relates to: (1) a preservative efficacy-enhancing agent for antiseptic agents which includes an amphiphilic galactose derivative (A) as an effective ingredient; (2) a preservative efficacy-enhancing composition including 0.01 to 30% by mass of an amphiphilic galactose derivative (A) and 0.01 to 1.0% by mass of an antiseptic agent (B); and (3) a method for enhancing a preservative efficacy of an antiseptic composition which includes the step of allowing 0.01 to 30% by mass of an amphiphilic galactose derivative (A) to coexist with an antiseptic agent (B) in the composition.

5 Claims, No Drawings

AGENT FOR ENHANCING ANTISEPTIC POWER

FIELD OF THE INVENTION

The present invention relates to preservative efficacy-enhancing agents, preservative efficacy-enhancing compositions containing the same, and a method for enhancing a preservative efficacy of antiseptic agents.

BACKGROUND OF THE INVENTION

In the products such as cosmetics, drugs, quasi-drugs and foods, in order to ensure antiseptic and mildew-proof properties of these products upon production and storage thereof, antiseptic agents such as p-oxybenzoic acid esters (also referred to merely as "parabenes"), benzoic acid and salts thereof, salicylic acid and salts thereof, 2-phenoxyethanol and polyhydric alcohols have been conventionally blended in the products.

Among these antiseptic agents, in particular, the parabenes have been generally used in the applications such as cosmetics because of a high effectiveness thereof. However, some users having a sensitive skin have frequently complained about irritating feel to skin against these antiseptic agents. Also, in the application fields such as cosmetics, there tends to be an increasing demand for products which are gentle and mild for skin and exhibit a still higher safety. For this reason, it has been attempted to reduce an amount of the antiseptic agents such as parabenes and 2-phenoxyethanol which are blended in the cosmetics, etc.

For example, there have been proposed the external preparations containing 1,2-pentanediol and 2-phenoxyethanol (JP 10-53510A); sterile power-enhancing agents having a cation charge which contain sugar alcohols and/or sugars as effective ingredients (JP 10-330793A); antiseptic bactericides using combination of parabenes and 1,2-alkane diols such as 1,2-pentanediol and 1,2-hexanediol (JP 11-310506A); antiseptic bactericides using 1,2-alkane diols or combination of the 1,2-alkane diols, parabenes, 2-phenoxyethanol, etc. (JP 11-322591A); antibacterial mildew-proof assistants using pentose or a sugar alcohol thereof as an effective ingredient (JP2002-302404A); and antiseptic compositions containing an antiseptic agent and 1,2-decanediol (JP 2004-352688A).

In addition, it is known that when 1,3-propanediol is used in combination with an antiseptic agent such as parabenes, an antibacterial glycerol derivative (such as, for example, monofatty acid glycerol esters and monofatty acid polyglycerol esters), a lower alcohol, etc., the amount of the antiseptic agent or antibacterial compound blended can be reduced (JP 2005-15401A).

Thus, there have been conventionally reported various methods for reducing the amount of antiseptic agents blended. However, even when the antiseptic agents are used in combination with other substances, the resultant compositions have still failed to exhibit a satisfactory effect of enhancing a preservative efficacy. Therefore, at present, there is no method for effectively reducing a total amount of the antiseptic agents used.

Also, it is known that when allowing parabenes to coexist with a surfactant, the parabenes are generally incorporated into micelle formed by the surfactant in water, thereby lowering an effective concentration thereof (inactivation phenomenon). The inactivation phenomenon of the parabenes is also recognized in an emulsion system such as an oil-in-water (O/W) emulsion. However, there has been conventionally present no method of effectively controlling or suppressing the inactivation phenomenon.

SUMMARY OF THE INVENTION

Thus, the present invention relates to the following aspects [1] to [3]:

[1] A preservative efficacy-enhancing agent for antiseptic agents, including an amphiphilic galactose derivative (A) as an effective ingredient;

[2] a preservative efficacy-enhancing composition including 0.01 to 30% by mass of an amphiphilic galactose derivative (A) and 0.01 to 1.0% by mass of an antiseptic agent (B); and

[3] a method for enhancing a preservative efficacy of an antiseptic composition, including the step of allowing 0.01 to 30% by mass of an amphiphilic galactose derivative (A) to coexist with an antiseptic agent (B) in the composition.

DETAILED DESCRIPTION OF THE INVENTION

The present invention relates to a preservative efficacy-enhancing agent capable of allowing the antiseptic agent to exhibit a high preservative efficacy when used at a low concentration in antiseptic systems requiring an antiseptic agent; a preservative efficacy-enhancing composition containing such a preservative efficacy-enhancing agent; and a method for enhancing a preservative efficacy of the antiseptic agent.

The present inventors have found that when an amphiphilic galactose derivative having no preservative efficacy by itself is used in combination with an antiseptic agent such as parabenes, the antiseptic agent can be remarkably enhanced in preservative efficacy and the amount of the antiseptic agent blended can be considerably reduced even in systems in which a surfactant inactivating the antiseptic agent is present, resulting in a less irritativeness and a sufficient antiseptic effect.

Thus, the present invention relates to:

[1] A preservative efficacy-enhancing agent for antiseptic agents, including an amphiphilic galactose derivative (A) as an effective ingredient;

[2] a preservative efficacy-enhancing composition including 0.01 to 30% by mass of an amphiphilic galactose derivative (A) and 0.01 to 1.0% by mass of an antiseptic agent (B); and

[3] a method for enhancing a preservative efficacy of an antiseptic composition, including the step of allowing 0.01 to 30% by mass of an amphiphilic galactose derivative (A) to coexist with an antiseptic agent (B) in the composition.

(Preservative Efficacy-Enhancing Agent)

The preservative efficacy-enhancing agent of the present invention contains an amphiphilic galactose derivative (A) as an effective ingredient. The "preservative efficacy-enhancing agent" used herein means those compounds having an effect of enhancing a preservative efficacy of an antiseptic agent when allowing the compounds to coexist with the antiseptic agent even though the compounds have no or very slight preservative efficacy by themselves.

Also, the "preservative efficacy" used herein means a defensive power against all contaminant organisms such as bacteria, mildew and yeast, and also involves a concept of mildew-proofing.

The amphiphilic galactose derivative (A) used in the present invention means such a galactose derivative having both of hydrophilic and hydrophobic properties. Specific examples of the amphiphilic galactose derivative include natural galactolipids containing a galactose residue at a terminal end thereof and analogues thereof, and synthetic galactolipids such as alkyl glycosides having a galactose residue at a terminal end thereof.

Examples of the natural galactolipids containing a galactose residue at a terminal end thereof and analogues thereof include glyceroglycolipids such as monogalactosyl diacyl glycerols (MGDG), digalactosyl diacyl glycerols (DGDG) and sulfoquinovosyl diacyl glycerols (SQDG), glycosyl ceramides such as galactosyl ceramide and lactosyl ceramide, and those compounds described in JP 6-80545A such as 3-(octyloxy)-2-hydroxypropyl-β-D-galactopyranoside and 3-(N,N-dibutylamino)-2-hydroxypropyl-β-D-galactopyranoside, and a mixture thereof.

Meanwhile, the "glyceroglycolipids" mean glycolipids having a glycerol skeletal structure which are hydrolyzed into sugars and lipids [refer to "Glyceroglycolipids of Photosynthetic Organisms—Their Biosynthesis and Evolutionary Origin—", Trends in Glycoscience and Glycotechnology, Vol. 12, No. 66, pp. 241 to 253 (Forum: Carbohydrates Coming of Age, July 2000)].

Among these galactose derivatives, preferred are alkyl galactosides represented by the following formula (1):

R-O-(G)n    (1)

wherein R is a linear or branched alkyl group having 6 to 36 carbon atoms which may be substituted; G is a galactose residue; and n is an integer of 1 to 20.

The alkyl galactosides represented by the above formula (1) are compounds in which one or more galactose residues are bonded to an alkyl group having 6 to 26 carbon atoms through an α- or β-glycoside linkage.

The alkyl group R in the above formula (1) may be either linear or branched, and has preferably 8 to 22 carbon atoms and more preferably 10 to 20 carbon atoms. Specific examples of the alkyl group R include n-hexyl, n-heptyl, n-octyl, n-decyl, n-dodecyl, n-tetradecyl, n-hexadecyl, n-octadecyl, isostearyl, 2-ethylhexyl, 2-hexyldecyl, 2-octyldodecyl and 2-decyltetradecyl.

Among these alkyl groups, in view of exhibiting a good effect as an antiseptic assistant, preferred are n-decyl, n-dodecyl, n-tetradecyl, n-hexadecyl, 2-hexyldecyl and 2-octyldodecyl.

The galactose residue may include any of a pyranose type, a furanose type and a mixture thereof.

The suffix n is preferably an integer of from 1 to 10 and more preferably from 1 to 6. The (G)n may be a monosaccharide, a disaccharide, a trisaccharide, a tetrasaccharide or the other oligosaccharide. The bonding type of these compounds may be either a maltose type or a trehalose type.

Suitable examples of the alkyl galactosides represented by the above formula (1) include α,β-n-decyl galactoside, α,β-n-dodecyl galactoside, α,β-n-tetradecyl galactoside, α,β-n-hexadecyl galactoside, α,β-2-hexyldecyl galactoside and α,β-2-octyldodecyl galactoside. These alkyl galactosides may be used alone or in combination of any two or more thereof.

The alkyl galactosides represented by the above formula (1) may be produced by the method of subjecting D-galactose sequentially to acetylation, halogenation, alcohol condensation and deacetylation [refer to Ryohei HORI and Yoshihiko IKEGAMI, "Studies on Carbohydrate Derivatives. V. Syntheses of Alkyl Galactosides and Alkyl Glycosides", Pharmaceutical Journal, Vol. 79, No. 1, pp. 80-83 (1959)], the method described below in Production Examples, etc. (Preservative Efficacy-Enhancing Composition and Method for Enhancing Preservative Efficacy)

The preservative efficacy-enhancing composition of the present invention contains 0.01 to 30% by mass of an amphiphilic galactose derivative (A) and 0.01 to 1.0% by mass of an antiseptic agent (B). Also, the method for enhancing a preservative efficacy according to the present invention is characterized by allowing 0.01 to 30% by mass of the above amphiphilic galactose derivative (A) to coexist with the antiseptic agent (B).

The "preservative efficacy-enhancing composition" used herein means such a composition containing the antiseptic agent whose preservative efficacy is enhanced by adding the amphiphilic galactose derivative (A) thereto.

The antiseptic agent (B) used in the present invention means those agents added to cosmetics, drugs, quasi-drugs, detergents, foods, etc., for the purpose of suppressing growth of microbes and preventing microbial deterioration of these products, and generally includes those ordinarily used as antiseptics as well as substances having antibacterial or bactericidal properties.

The antiseptic agent (B) usable in the present invention is not particularly limited, and may be known antiseptics. Examples of the antiseptic agent (B) include, in addition to p-oxybenzoic esters (parabenes), benzoic acid, salicylic acid, sorbic acid, dehydroacetic acid, p-toluenesulfonic acid and salts thereof, and phenoxyethanol.

The p-oxybenzoic esters (parabenes) are lower alkyl esters thereof containing an alkyl group having 1 to 4 carbon atoms. Examples of the p-oxybenzoic esters (parabenes) include methyl p-oxybenzoate (methyl parabene), ethyl p-oxybenzoate (ethyl parabene) and butyl p-oxybenzoate (butyl parabene). The salts of benzoic acid, salicylic acid, sorbic acid, dehydroacetic acid and p-toluenesulfonic acid are alkali metal salts and preferably sodium salts.

These antiseptic agents (B) may be used alone or in combination of any two or more thereof.

Among these antiseptic agents (B), in view of enhancing a preservative efficacy thereof when used in combination with the amphiphilic galactose derivative (A), preferred are p-oxybenzoic esters, benzoic acid, alkali metal salts of benzoic acid and phenoxyethanol, and in view of a reduced amount of the antiseptic agent used and a low irritativeness to skin, more preferred are one or more compounds selected from the group consisting of p-oxybenzoic esters such as methyl p-oxybenzoate and ethyl p-oxybenzoate, and 2-phenoxyethanol.

Examples of the substances having antibacterial or bactericidal properties include glycerol derivatives, alkane diols and lower alcohols.

Specific examples of the glycerol derivatives include monofatty acid glycerol esters, monofatty acid polyglycerol esters and monoalkyl glyceryl ethers.

The monofatty acid glycerol esters are preferably monoglycerol esters of saturated fatty acids having 6 to 14 carbon atoms and preferably 8 to 12 carbon atoms. Examples of the monofatty acid glycerol esters include monocaprylic acid glycerol ester, monocapric acid glycerol ester and monolauric acid glycerol ester.

The monofatty acid polyglycerol esters are preferably esters of a saturated fatty acid having 6 to 14 carbon atoms and preferably 8 to 12 carbon atoms and polyglycerol (having a polymerization degree of 2 to 12 and preferably 3 to 10). Examples of the monofatty acid polyglycerol esters include monolauric acid pentaglycerol ester and monolauric acid decaglycerol ester.

Examples of the monoalkyl glyceryl ethers include monooctyl glyceryl ether and mono-2-ethylhexyl glyceryl ether.

Among these compounds, especially preferred are monocaprylic acid glycerol ester, monocapric acid glycerol ester, monolauric acid decaglycerol ester, monolauric acid pentaglycerol ester and monooctyl glyceryl ether.

The alkane diols are preferably those having 2 to 12 carbon atoms. Examples of the alkane diols include ethanediol, 1,2-propanediol, 1,3-propanediol, 1,2-butanediol, 1,3-butanediol, 1,4-butanediol, 2,3-butanediol, 1,6-hexanediol and 1,12-dodecanediol. Among these alkane diols, especially preferred are those having 2 to 6 carbon atoms.

The lower alcohols are preferably those alcohols having 1 to 4 carbon atoms. Examples of the lower alcohols include ethanol, n-propanol, isopropanol and various kinds of butanols.

The content of the amphiphilic galactose derivative (A) used in the preservative efficacy-enhancing composition and the method for enhancing a preservative efficacy according to the present invention, is from 0.01 to 30% by mass, preferably from 0.05 to 5% by mass and more preferably from 0.05 to 2% by mass.

The amount of the antiseptic agent (B) blended in the preservative efficacy-enhancing composition may be appropriately determined according to features of commercial products and a necessary preservative efficacy therefore, and is usually from 0.01 to 1.0% by mass and preferably from 0.05 to 0.8% by mass. In the present invention, by using the antiseptic agent (B) in combination with the amphiphilic galactose derivative (A), an adequate preservative efficacy can be maintained, and the amount of the antiseptic agent used can be considerably reduced. Therefore, the preservative efficacy-enhancing composition of the present invention can be used in relief and with a high safety even when applied to persons having a sensitive skin.

In general, an effectiveness of antiseptics tends to be considerably deteriorated in the presence of a nonionic surfactant. However, in the preservative efficacy-enhancing composition and the method for enhancing a preservative efficacy according to the present invention, by blending an adequate amount of the nonionic surfactant together with the amphiphilic galactose derivative (A) and the antiseptic agent (B) in the composition, a remarkable effect of suppressing deterioration of the preservative efficacy can be attained, thereby maintaining a high preservative efficacy.

The nonionic surfactant usable in the present invention may include ordinary nonionic surfactants. Examples of the nonionic surfactant include alkyleneoxide adducts such as polyoxyethylene alkyl ethers, polyoxyethylene hydrogenated castor oil, fatty acid polypropylene glycol esters and fatty acid polyoxyethylene glycol esters, and polyol fatty acid esters such as fatty acid sucrose esters, fatty acid glycerol esters, fatty acid sorbitan esters and fatty acid polyglycerol esters.

The amount of the nonionic surfactant (C) blended may be appropriately determined depending upon the preservative efficacy required for the antiseptic agent (B). In the composition containing from 0.01 to 30% by mass of the amphiphilic galactose derivative (A) and from 0.01 to 1.0% by mass of the antiseptic agent (B), the amount of the nonionic surfactant (C) blended therein is usually from 0.01 to 50% by mass and preferably from 0.1 to 30% by mass.

The preservative efficacy-enhancing agent and the preservative efficacy-enhancing composition of the present invention can be effectively applied to various extensive compositions and products requiring a preservative efficacy. Examples of the compositions and products include foundation cosmetics, make-up cosmetics, other cosmetics such as hair cosmetics, drugs such as external preparations for skin, quasi-drugs, detergents, foods, etc.

Further, the preservative efficacy-enhancing agent and the preservative efficacy-enhancing composition of the present invention may also contain adequate amounts of other components and additives ordinarily added thereto, such as, for example, liquid or solid oils, higher fatty acids, alcohols, surfactants, thickening agents, pH modifiers, humectants, colorants and perfumes depending upon the applications thereof, unless the addition thereof adversely affects the objects of the present invention.

The configuration of the preservative efficacy-enhancing agent and the preservative efficacy-enhancing composition of the present invention upon use is not particularly limited. The preservative efficacy-enhancing agent and the preservative efficacy-enhancing composition of the present invention may be used in various configurations such as an aqueous solution system, a solubilized system, an emulsified system, a gel system, a paste system, an ointment system, an air-sol system, a water-oil two-layer system and a water-oil-powder three-layer system.

EXAMPLES

Production Example 1

Production of α,β-n-dodecyl galactoside

D-galactose and n-dodecyl alcohol were reacted with each other while heating and dehydrating under reduced pressure in the presence of a catalytic amount of p-toluenesulfonic acid monohydrate. The resultant mixture was purified by a silica gel column, thereby obtaining n-dodecyl galactoside having a galactose condensation degree of 1 to 3. As a result of analyzing the obtained product by gel permeation chromatography, gas chromatography and $^1$H-NMR, it was confirmed that the thus obtained α,β-n-dodecyl galactoside had an average sugar condensation degree of 1.48, and the n-dodecyl monogalactoside component thereof had such a composition in which a molar ratio of pyranoside to furanoside (pyranoside/furanoside) was 83/17, and a molar ratio of α-pyranoside to β-pyranoside (α/β) in the component was 75/25.

Production Example 2

Production of α,β-2-hexyldecyl galactoside

The same procedure as in Production Example 1 was repeated except for using hexyldecyl alcohol as the raw material, thereby obtaining α,β-2-hexyldecyl galactoside.

Example 1 and Comparative Examples 1 and 2

Antiseptic Composition

Using the α,β-n-dodecyl galactoside obtained in Production Example 1, the antiseptic compositions (pH: 6.5) having the formulation (% by mass) shown in the following Table 1 were respectively prepared, and then subjected to the following antibacterial test. The results are shown in Table 1.

Antibacterial Test

The following bacteria were suspended in a physiological saline such that the number of bacteria or spores was $10^8$ CFU/mL. to prepare a bacteria-containing solution. Then, 0.005 mL of the thus obtained bacteria-containing solution was inoculated into 5 mL of the composition to be tested such that the bacteria concentration therein was $10^8$ CFU/mL. The thus inoculated composition was held at 30° C. for a predetermined period of time to measure the change in number of bacteria with time by the calculation using a colony counting method. The antibacterial property of the composition was evaluated according to the following four ratings.

Kinds of Bacteria Used
*Staphylococcus aureus* IFO13276
*Escherichia coli* IFO3972
*Pseudomonas aeruginosa* IFO13275

Evaluation Criteria for Antibacterial Properties
⊚: Sufficiently high antibacterial property (number of bacteria was decreased by $10^4$ or more)
○: High antibacterial property (number of bacteria was decreased by $10^3$ to $10^2$)
Δ: Low antibacterial property (number of bacteria was decreased by $10^2$ to $10^1$)
X: No antibacterial property (number of bacteria was substantially unchanged or rather increased)

TABLE 1

|  | Example 1 | Comparative Example 1 | Comparative Example 2 |
|---|---|---|---|
| Methyl p-oxybenzoate | 0.075 | 0.075 | — |
| α,β-n-dodecyl galactoside | 0.1 | — | 0.1 |
| Purified water | Balance | Balance | Balance |
| Evaluation of antibacterial property after 9 days | ⊚ | Δ | X |

From the results shown in Table 1, it was confirmed that (α,β-n-dodecyl galactoside having an amphiphilic property exhibited no antibacterial property by itself, but was capable of enhancing a preservative efficacy of the antiseptic agent (methyl p-oxybenzoate) when used in combination therewith.

Example 2 and Comparative Examples 3 to 6

Antiseptic Composition

Using the α,β-2-hexyldecyl galactoside obtained in Production Example 2, the antiseptic compositions (pH: 6.5) having the formulation (% by mass) shown in the following Table 2 were respectively prepared, and then subjected to the antibacterial test in the same manner as in Example 1. The results are shown in Table 2.

TABLE 2

|  | Example | Comparative Examples | | | |
|---|---|---|---|---|---|
|  | 2 | 3 | 4 | 5 | 6 |
| Methyl p-oxybenzoate | 0.15 | 0.15 | 0.15 | — | 0.15 |
| α,β-2-hexyldecyl galactoside | 0.1 | — | — | 0.1 | — |
| Polyoxyethylene (60) hydrogenated castor oil | 1.0 | — | 1.0 | 0.1 | 1.0 |
| α,β-2-hexyldecyl glycoside | — | — | — | — | 0.1 |
| Purified water | Balance | Balance | Balance | Balance | Balance |
| Evaluation of antibacterial property after 7 days | ⊚ | ○ | Δ | X | Δ |

From the results shown in Table 2, it was confirmed that α,β-2-hexyldecyl galactoside having an amphiphilic property exhibited no antibacterial property by itself, but was capable of specifically enhancing a preservative efficacy of the antiseptic agent (methyl p-oxybenzoate) inactivated by the nonionic surfactant (polyoxyethylene (60) hydrogenated castor oil) when used in combination with the antiseptic agent.

Example 3 and Comparative Examples 7 to 9

Antiseptic Composition

Using the α,β-2-hexyldecyl galactoside obtained in Production Example 2, the antiseptic compositions (pH: 6.5) having the formulation (% by mass) shown in the following Table 3 were respectively prepared, and then subjected to the following antiseptic test. The results are shown in Table 3.

Antiseptic Test

The following microbe were suspended in a physiological saline such that the number of microbe or spores was $10^8$ CFU/mL. to prepare a microbe-containing solution. Then, 0.005 mL of the thus obtained microbe-containing solution was inoculated into 50 g of the composition to be tested such that the microbe concentration therein was $10^8$ CFU/mL. The inoculated composition was held at 30° C. for 28 days to measure the change in number of microbe with time by the calculation using a colony counting method. The antiseptic property of the antiseptic composition was evaluated according to the following four ratings.

Kinds of Microbe Used
*Staphylococcus aureus* IFO13276
*Escherichia coli* IFO3972
*Pseudomonas aeruginosa* IFO13275
*Aspergillus niger* IFO6341
*Penicillium citrinum* IFO6352
*Cladosporium cladosporoides* IFO6348

Evaluation Criteria for Antiseptic Properties
⊚: High antiseptic property
○: Some antiseptic property
Δ: Substantially no antiseptic property
X: No antiseptic property

TABLE 3

|  | Example 3 | Comparative Examples | | |
|---|---|---|---|---|
|  |  | 7 | 8 | 9 |
| Methyl p-oxybenzoate | 0.2 | 0.2 | 0.2 | 0.2 |
| α,β-2-hexyldecyl galactoside | 0.1 | — | — | — |
| Polyoxyethylene (60) hydrogenated castor oil | 0.5 | 0.5 | 1.0 | 0.1 |
| Galactose | — | 0.1 | — | — |
| Lactose | — | — | 0.1 | — |
| Extract of *thujopsis* (hiba arborvitae) | 3.0 | 3.0 | 3.0 | 3.0 |
| Purified water | Balance | Balance | Balance | Balance |
| Evaluation of antiseptic property | ⊚ | Δ | Δ | Δ |

From the results shown in Table 3, it was confirmed that only α,β-2-hexyldecyl galactoside having an amphiphilic property was capable of enhancing a preservative efficacy of the antiseptic agent (methyl p-oxybenzoate).

Examples 4 and 5 and Comparative Examples 10 and 11

Antiseptic Composition

Using the α,β-2-hexyldecyl galactoside obtained in Production Example 2, the antiseptic compositions (pH: 6.5)

having the formulation (% by mass) shown in the following Table 4 were respectively prepared, and then subjected to the antibacterial test in the same manner as in Example 1. The results are shown in Table 4.

TABLE 4

| | Example 4 | Comparative Example 10 | Example 5 | Comparative Example 11 |
|---|---|---|---|---|
| Methyl p-oxybenzoate | 0.15 | 0.15 | 0.15 | 0.15 |
| α,β-2-hexyldecyl galactoside | 0.1 | — | 0.1 | — |
| Polyoxyethylene octyldodecyl ether | 1.0 | 1.0 | — | — |
| EMALEX RWIS-160*[1] | — | — | 1.0 | 1.0 |
| Purified water | Balance | Balance | Balance | Balance |
| Evaluation of antibacterial property after 10 days | ◯ | X | ◎ | X |

Note
*[1]Nonionic surfactant available from Nihon Emulsion Co., Ltd.; polyoxyethylene monoisostearate hydrogenated castor oil (40 E.O.).

From the results shown in Table 4, it was confirmed that α,β-2-hexyldecyl galactoside having an amphiphilic property was capable of enhancing a preservative efficacy of the antiseptic agent (methyl p-oxybenzoate) inactivated by the nonionic surfactant (EMALEX RWIS-160).

Example 6 and Comparative Examples 12 to 14

Using the α,β-2-hexyldecyl galactoside obtained in Production Example 2, the milky lotions (emulsions) having the formulation (% by mass) shown in the following Table 5 were respectively prepared by the following method. The resultant milky lotions were held at a pH of 6.5 and 30° C. for 14 days, and then subjected to an antiseptic test in the same manner as in Example 3. The results are shown in Table 5.
(Production of Milky Lotions)
A solution prepared by dissolving the component (10) in the component (9) at room temperature was added to an aqueous solution prepared by uniformly dissolving the components (11) to (15), (17) and (18) under heating. The obtained solution was slowly added to a solution prepared by dissolving the components (1) to (8) and (16) under heating. The resultant mixed solution was stirred using a homomixer, and then cooled to prepare a milky lotion.

TABLE 5

| | | | Comparative Examples | | |
|---|---|---|---|---|---|
| | Formulation | Example 6 | 12 | 13 | 14 |
| 1 | Sodium polyoxyethylene lauryl ether phosphate | 0.6 | 0.6 | 0.6 | 0.6 |
| 2 | Sorbitan monostearate | 0.3 | 0.3 | 0.3 | 0.3 |
| 3 | Sodium N-stearoyl-N-methyl taurine | 0.8 | 0.8 | 0.8 | 0.8 |
| 4 | Polyglyceryl diisostearate | 1.0 | 1.0 | 1.0 | 1.0 |
| 5 | Olive oil | 2.0 | 2.0 | 2.0 | 2.0 |
| 6 | Squarane | 0.5 | 0.5 | 0.5 | 0.5 |
| 7 | Cetyl alcohol | 1.0 | 1.0 | 1.0 | 1.0 |
| 8 | Stearyl alcohol | 0.5 | 0.5 | 0.5 | 0.5 |
| 9 | Methyl polysiloxane (6 CS) | 5.0 | 5.0 | 5.0 | 5.0 |
| 10 | Glycerol | 15 | 15 | 15 | 15 |
| 11 | Carboxyvinyl polymer *[3] | 0.2 | 0.2 | 0.2 | 0.2 |
| 12 | Succinic acid | 0.01 | 0.01 | 0.01 | 0.01 |
| 13 | Potassium hydroxide | 0.07 | 0.07 | 0.07 | 0.07 |
| 14 | Methyl p-oxybenzoate | 0.3 | 0.3 | 0.3 | 0.3 |
| 15 | 1,3-Butylene glycol | 3.0 | 3.0 | 3.0 | 3.0 |
| 16 | α,β-2-hexyldecyl galactoside | 0.1 | — | — | — |
| 17 | Galactose | — | — | 0.1 | — |
| 18 | Lactose | — | — | — | 0.1 |
| 19 | Purified water | Balance | Balance | Balance | Balance |
| | Evaluation of antiseptic property | ◎ | Δ | Δ | Δ |

Note
*[3] "CARBOPOLE 981" (tradename) available from Noveon Inc.

From the results shown in Table 5, it was confirmed that the α,β-2-hexyldecyl galactoside having an amphiphilic property was capable of enhancing a preservative efficacy of the milky lotion, and the obtained milky lotion had a less irritativeness to skin.

Example 7 and Comparative Example 15

Using the α,β-2-hexyldecyl galactoside obtained in Production Example 2, the emulsions having the formulation (% by mass) shown in the following Table 6 were respectively prepared by the following method. The resultant emulsions were held at a pH of 6.5 and 30° C. for 14 days, and then subjected to an antiseptic test in the same manner as in Example 3. The results are shown in Table 6.
(Production of Cream)
A solution prepared by dissolving the component (12) in the component (11) at room temperature was added to an aqueous solution prepared by uniformly dissolving the components (13) to (18) and (20) under heating. The obtained solution was slowly added to a solution prepared by dissolving the components (1) to (10) and (19) under heating. The resultant mixed solution was stirred using a homomixer, and then cooled to prepare a emulsion.

TABLE 6

| | Formulation | Example 7 | Comparative Example 15 |
|---|---|---|---|
| 1 | N-(hexadecyloxy-hydroxypropyl)-N-hydroxyethyl hexadecanamide | 3.0 | 3.0 |
| 2 | Polyoxyethylene sorbitan monostearate (20 E.O.) | 0.4 | 0.4 |
| 3 | Sorbitan monostearate | 0.6 | 0.6 |
| 4 | Sodium polyoxyethylene lauryl ether phosphate | 0.6 | 0.6 |
| 5 | Polyglycerol diisostearate | 2.0 | 2.0 |
| 6 | Cholesteryl isostearate | 10.0 | 10.0 |
| 7 | Cetanol | 1.5 | 1.5 |
| 8 | Stearyl alcohol | 1.0 | 1.0 |
| 9 | Squarane | 3.0 | 3.0 |
| 10 | Dipropylene glycol | 3.0 | 3.0 |
| 11 | Methyl polysiloxane (10 CS) | 5.0 | 5.0 |
| 12 | Glycerol | 15.0 | 15.0 |
| 13 | Carboxyvinyl polymer *[3] | 0.5 | 0.5 |

TABLE 6-continued

| | Formulation | Example 7 | Comparative Example 15 |
|---|---|---|---|
| 14 | Potassium hydroxide | 0.25 | 0.25 |
| 15 | Methyl p-oxybenzoate | 0.3 | 0.3 |
| 16 | Extract of brown aglae (phaeophyceace) | — | 0.2 |
| 17 | Extract of burnet | — | 0.3 |
| 18 | Extract of *thujopsis* (hiba arborvitae) | — | 1.0 |
| 19 | α,β-2-hexyldecyl galactoside | 0.1 | — |
| 20 | Perfume | trace | trace |
| 21 | Purified water | Balance | Balance |
| | Evaluation of antiseptic property | ○ | X |

Note
*[3] "CARBOPOLE 981" (tradename) available from Noveon Inc.

From the results shown in Table 6, it was confirmed that the emulsion obtained in Example 7 which contained α,β-2-hexyldecyl galactoside having an amphiphilic property exhibited a strong preservative efficacy, and the resultant emulsion had a less irritativeness to skin.

INDUSTRIAL APPLICABILITY

In accordance with the present invention, when the amphiphilic galactose derivative is allowed to coexist with an antiseptic agent such as parabenes, an preservative efficacy of the antiseptic agent can be remarkably enhanced, and a total amount of the antiseptic agent used can be effectively reduced. Also, even when the antiseptic agent is used at a low concentration and a surfactant coexists therewith, it is possible to allow the antiseptic agent to exhibit a sufficient preservative efficacy and; as a result, obtain products having a low irritativeness to skin.

What is claimed is:

1. A preservative efficacy-enhancing composition for an antiseptic composition, said preservative efficacy-enhancing composition comprising:
    0.01 to 2% by mass of an amphiphilic galactose derivative (A) as an effective ingredient; and
    0.01 to 1.0% by mass of an antiseptic agent (B):
    wherein the amphiphilic galactose derivative (A) is at least one compound selected from the group consisting of α,β-n-decyl galactoside, α,β-n-dodecyl galactoside, α,β-n-tetradecyl galactoside, α,β-n-hexadecyl galactoside, α,β-2-hexyldecyl galactoside, and α,β-2-octyl-dodecyl galactoside;
    wherein the antiseptic agent (B) is one or more selected from the group consisting of p-oxybenzoic ester, benzoic acid, and phenoxyethanol; and
    wherein the amphiphilic galactose derivative (A) enhances a preservative efficacy of the antiseptic agent (B) in the preservative efficacy-enhancing composition.

2. The preservative efficacy-enhancing composition according to claim 1, further comprising 0.01 to 50% by mass of a nonionic surfactant (C).

3. The preservative efficacy-enhancing composition according to claim 2, wherein the nonionic surfactant (C) is at least one compound selected from the group consisting of polyoxyethylene alkyl ethers, polyoxyethylene hydrogenated castor oil, fatty acid polypropylene glycol esters, fatty acid polyoxyethylene glycol esters, fatty acid sucrose esters, fatty acid glycerol esters, fatty acid sorbitan esters and fatty acid polyglycerol esters.

4. A cosmetic, drug, quasi-drug, detergent or food comprising the preservative efficacy-enhancing composition as defined in claim 1.

5. A cosmetic, drug, quasi-drug, detergent or food comprising the preservative efficacy-enhancing composition according to claim 2.

* * * * *